United States Patent [19]

Hyman

[11] Patent Number: 5,840,575
[45] Date of Patent: Nov. 24, 1998

[54] DNA LADDERS

[76] Inventor: Edward David Hyman, Bayou Biolabs 1500 Edwards Ave. suite Q, Harahan, La. 70123

[21] Appl. No.: 781,866

[22] Filed: Jan. 10, 1997

[51] Int. Cl.$^6$ .............................. C12N 15/63; C12Q 1/68; C07H 21/04
[52] U.S. Cl. ........................... 435/320.1; 435/6; 536/23.1
[58] Field of Search ..................... 435/6, 320.1; 536/23.1

[56] References Cited

U.S. PATENT DOCUMENTS 4,403,036   9/1983   Hartley ..................................... 435/317

*Primary Examiner*—George C. Elliott
*Assistant Examiner*—Andrew Wang

[57] ABSTRACT

DNA ladders are constructed by partial restriction digestion of plasmids with the following design properties: (a) the plasmid contains five or more sites of a restriction endonuclease; (b) the length between adjacent sites is an integer multiple of a minimal length, said minimal length is the length between the closest adjacent sites; (c) partial restriction endonuclease digestion of the plasmid generates a DNA ladder with at least five differently sized DNA fragments; and (d) said DNA ladder has the properties that (1) all DNA fragments of the ladder have lengths which are integer multiples of the minimal length; (2) the smallest DNA fragment length is the minimal length, (3) the largest DNA fragment is the length of the entire plasmid; and (4) the ladder has a DNA fragment at every integer multiple of the minimal length ranging from the minimal length to the plasmid length. This plasmid design is especially useful for making small fragment DNA ladders, such as 100 and 200 base pair ladders. In this case, the restriction sites are advantageously equally spaced from each other.

7 Claims, 4 Drawing Sheets

DNA LADDERS

BACKGROUND OF THE INVENTION

DNA ladders are common reagents in molecular biology, useful for determining the size of DNA fragments. A DNA ladder comprises two or more DNA fragments of known size. Typically, a DNA sample and a DNA ladder are loaded in adjacent wells of an agarose gel. The DNA is separated by electrophoresis through the gel. The gel is stained with a fluorescent dye, such as ethidium bromide, and exposed to ultraviolet light. The size of the sample DNA fragments are determined by comparing their migration with the bands of known size in the DNA ladder. DNA ladders are commercially available from numerous vendors, including Sigma, Pharmacia, Life Technologies, Promega, Boerhinger-Mannheim, Amersham, New England Biolabs, Stratagene, and Invitrogen.

One established method for manufacturing a DNA ladder is by partial restriction digestion of a special plasmid. The special plasmid contains an insert of tandem repeats of a DNA fragment. The same unique restriction site lies at each junction of the repeat units. Partial restriction digestion of this plasmid produces a ladder containing multimers of the repeated DNA fragment. For example, assume that a special plasmid contains an insert with the following characteristics: (i) the insert consists of a ten tandem repeat of a 100 base pair (bp) DNA fragment, (ii) the tandem repeat units are joined to each other and to the cloning vector by AvaI restriction sites. Partial restriction digestion with AvaI would produce a DNA ladder with fragments from 100 bp to 1,000 bp in 100 bp increments.

Constructing special plasmids of this type is established in the art. Such a plasmid is constructed by cloning multiple monomer DNA fragments in tandem into a cloning vector. Typically, the vector is pUC18, which is 2,686 bp. In the tandem repeat, the monomer fragments are usually oriented in a head to tail manner by using the cloning method of Hartley (U.S. Pat. No. 4,403,036). In Hartley's method, the monomer DNA fragment contains AvaI sites at each end which force polymerization to occur in a head to tail manner. The head to tail orientation improves plasmid stability, but it is not essential for the method of ladder production.

There are three problems with the established approach.

(1) Only the portion of the plasmid containing the tandem repeat can generate the ladder. The vector portion of the plasmid is not used to generate the ladder.

(2) The size of the largest DNA fragment in the ladder is limited to the size of the tandem repeat region.

(3) Restriction fragments containing the vector region of the plasmid produce a large smear of by-product fragments in the upper portion of the ladder. This upper smear does not contribute useful bands to the ladder.

Thus, it is well established in the art that ladders can be produced by partial restriction digestion of plasmids which contain tandem repeats of a DNA fragment. It is also well established that such ladders suffer three drawbacks: (1) Only the tandem repeat portion of the plasmid generates the ladder, (2) the largest DNA fragment is limited to the size of the tandem repeat, and (3) the upper bands containing the vector region of the plasmid do not contribute useful bands to the ladder. In this context, a useful approach to solve all these problems has been devised by the inventor.

OBJECTS OF THE INVENTION

Accordingly, the object of this invention is to provide plasmids for generating DNA ladders, (1) utilizing the entire plasmid to generate useful DNA fragments, (2) having a maximum fragment size equal to the entire plasmid size, and (3) not producing a by-product region of upper bands. Further objects and advantages will become apparent from a consideration of the drawings and ensuing description.

SUMMARY OF THE INVENTION

In accordance with the invention, there is provided a plasmid design for generating DNA ladders, whereby:

(a) the plasmid contains five or more R sites of a restriction endonuclease R;

(b) the length between adjacent R sites is an integer multiple of the minimal length, said minimal length is the length between the closest adjacent R sites;

(c) partial R restriction endonuclease digestion of the plasmid generates a DNA ladder with at least five differently sized DNA fragments; and (d) said DNA ladder has the properties that (i) all DNA fragments of the ladder have lengths which are integer multiples of the minimal length; (ii) the smallest DNA fragment length is the minimal length, (iii) the largest DNA fragment is the length of the entire plasmid; and (iv) the ladder has a DNA fragment at every integer multiple of the minimal length ranging from the minimal length to the plasmid length.

Preferably, most of the restriction sites are equally spaced from each other.

DETAILED DESCRIPTION OF THE INVENTION

The art of making DNA ladders from plasmids is well established. This is accomplished by constructing a plasmid containing a tandem repeat of a DNA insert. The DNA insert either contains a unique restriction site or is joined to each other by a unique restriction site. Partial digestion with this restriction endonuclease produces a DNA ladder containing multimers of the DNA insert.

The invention described herein is an improvement in the art of ladder production. The invention overcomes the drawbacks of previous approaches by using an improved plasmid design. As a result of the improved design, the entire plasmid produces useful fragments for the ladder.

In the invention, the plasmid is designed with the following properties:

(1) the plasmid contains five or more sites of a restriction endonuclease;

(2) the length between adjacent sites is an integer multiple of a minimal length, said minimal length is the length between the closest adjacent sites;

(3) partial restriction endonuclease digestion of the plasmid generates a DNA ladder with at least five differently sized DNA fragments; and (4) the DNA ladder has the properties that (i) all DNA fragments of the ladder have lengths which are integer multiples of the minimal length; (ii) the smallest DNA fragment length is the minimal length, (iii) the largest DNA fragment is the length of the entire plasmid; and (iv) the ladder has a DNA fragment at every integer multiple of the minimal length ranging from the minimal length to the plasmid length.

Ladders which satisfy these criteria utilize the entire plasmid to generate useful DNA fragments. The fragments form a stepped ladder from the minimal length to the maximum length. The maximum length is the entire plasmid size. Furthermore, there are no interruptions in the bands from the minimum to maximum sized bands.

Figure 1:
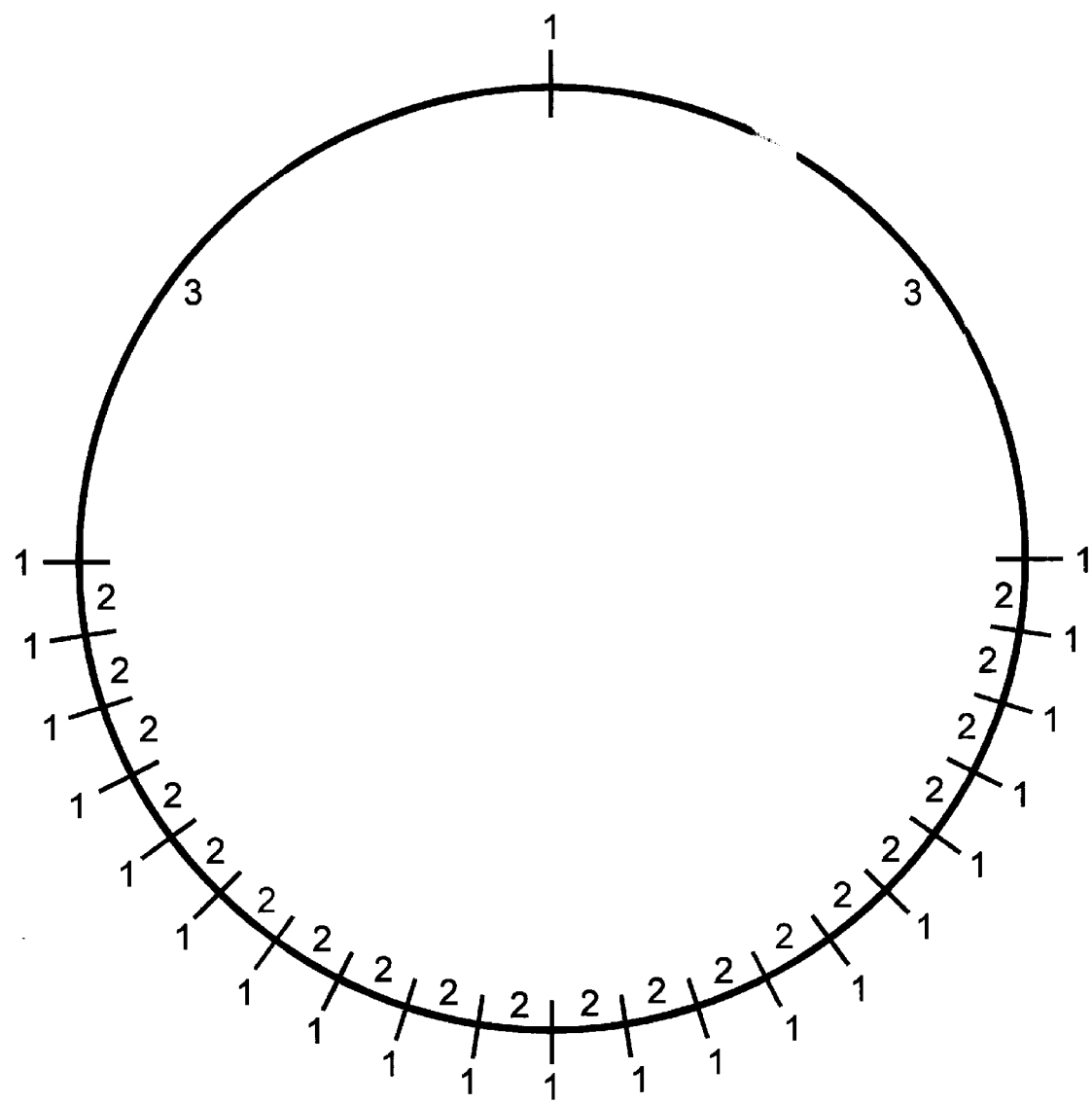
FIG. 1: A plasmid design for making a 100 bp DNA ladder.
Figure 2A:
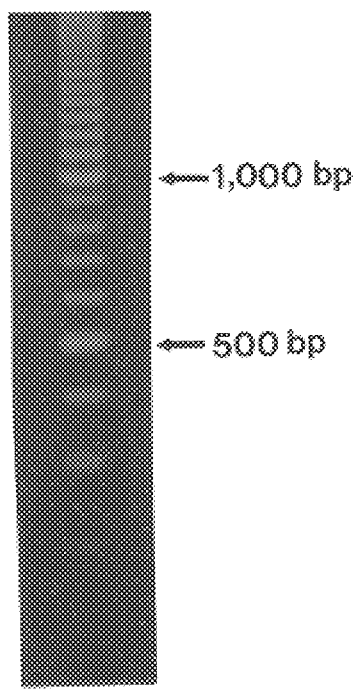
FIG. 2: Electrophoresis gels stained with ethidium bromide showing the DNA ladder produced by partial restriction digestion of the plasmid shown in FIG. 1. The ladder is spiked with a 500 bp fragment to help fragment identification. Part A shows a 2% Metaphor agarose gel of the 100 bp DNA ladder. Part B shows a 1% agarose gel of the 100 bp ladder with a 1 kilobase (kb) DNA ladder in the adjacent lane.
Figure 2B:
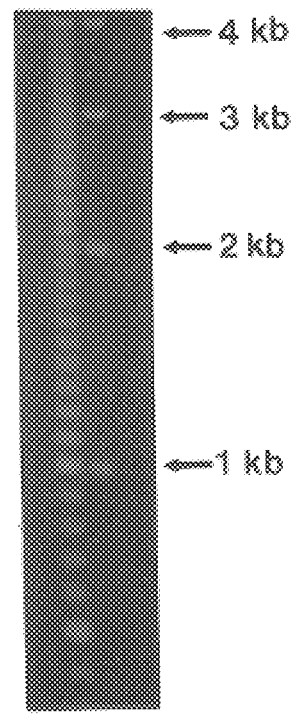

FIG. 1 illustrates a plasmid design which satisfies these four criteria of the invention. The plasmid contains 22 PvuII restriction sites, shown as hash marks "1". Twenty-one of the PvuII sites are located at a distance "2" of 100 bases apart. There is another PvuII site located a distance "3" of 1,000 bp from both adjacent sites. Partial PvuII digestion produces a 100 bp DNA ladder. The ladder contains 40 DNA fragments from 100 bp to 4,000 bp in 100 bp increments. Construction of this plasmid design is described in example 1 below. This plasmid of FIG. 1 produces a 100 base pair (bp) DNA ladder by partial PvuII restriction endonuclease digestion. The resulting 100 bp ladder is shown in FIG. 2. FIG. 2 shows electrophoretic gels separating the DNA fragments of the ladder. A small amount of a 500 bp fragment was added to the ladder to help identify the bands. Both gels were stained with ethidium bromide and viewed by ultraviolet illumination. FIG. 2A shows a 2% Metaphor agarose gel of the ladder. DNA fragments from 100 bp to 2,000 bp are visible and well resolved. FIG. 2B shows a 1% agarose gel of the 100 bp ladder in the left lane. DNA fragments from 400 bp to 4,000 bp visible are visible and well resolved. The right lane of the ladder shows a 1 kilobase (kb) DNA ladder, to help identify bands.

From FIG. 1, it can be seen that the plasmid design satisfies the criteria set forth above. Specifically, (1) there are more than five PvuII restriction sites, (2) the length between adjacent PvuII sites is an integer multiple of 100 bp, (3) partial PvuII digestion produces more than five differently sized DNA fragments, and (4) the fragments range from 100 bp to 4,000 bp in 100 bp increments.

As seen in the gel photos of FIG. 2, the band intensity increases at 1,000 bp. This is due to the fact that bands at 1,000 bp and above are also produced by fragments containing the 2 kb vector region. In general, large regions not containing restriction sites will produce a slight increase in intensity of the bands containing this region. This is a convenient outcome, as the differential band intensity facilitates the identification of bands on the gel. In the case of the 100 bp ladder of FIG. 2, band intensity is conveniently stepped. Each of the following band groups have about the same intensity: 100 bp–900 bp; 1,000 bp–1,900 bp; and 2,000 bp–4,000 bp. However, the intensity increases from the smallest band group to the largest band group. The stepped band intensity facilitates band identification.

Figure 3:
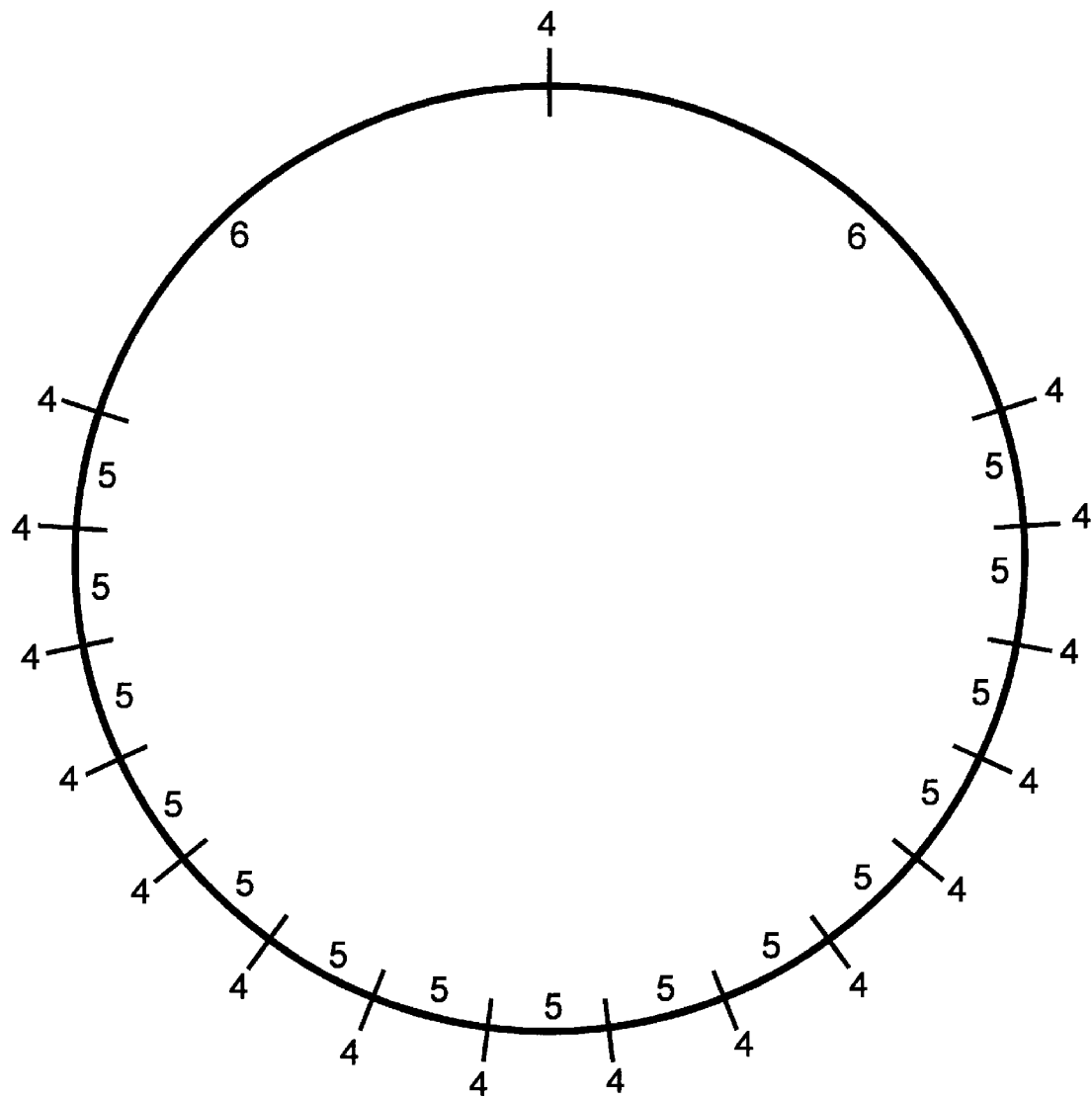
FIG. 3: A plasmid design for making a 200 bp DNA ladder.
Figure 4A:
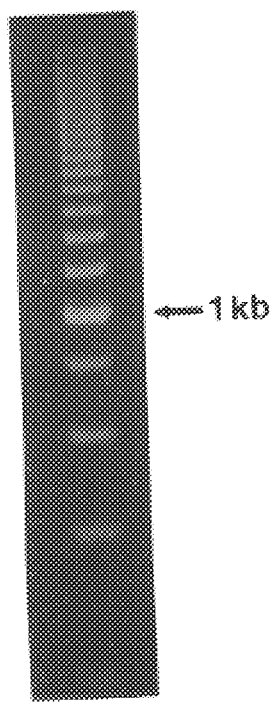
FIGS. 4A & 4B: Electrophoresis gels stained with ethidium bromide showing the DNA ladder produced by partial restriction digestion of the plasmid shown in FIG. 3. The ladder is spiked with a 1,000 bp fragment to help fragment identification. 4A shows a 2% Metaphor agarose gel of the 200 bp DNA ladder. 4B shows a 1% agarose gel of the 200 bp ladder with a 1 kilobase (kb) ladder in the adjacent lane.
Figure 4B:
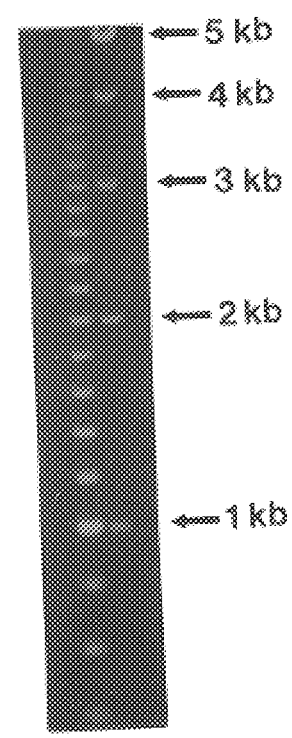

A second example of the invention is the plasmid design shown in FIG. 3. This plasmid design also satisfies the above criteria. The plasmid contains 17 PvuII restriction sites, shown as hash marks "4". Sixteen of the PvuII sites are located at a distance "5" of 200 bases apart. There is another PvuII site located a distance "6" of 1,000 bp from both adjacent sites. Partial PvuII digestion produces a 200 bp DNA ladder. The ladder contains 25 DNA fragments from 200 bp to 5,000 bp in 200 bp increments. Construction of this plasmid design is described in example 2 below. This plasmid of FIG. 3 produces a 200 base pair (bp) DNA ladder by partial PvuII restriction endonuclease digestion. The resulting 200 bp ladder is shown in FIG. 4. FIG. 4 shows electrophoretic gels separating the DNA fragments of the ladder. A small amount of a 1 kilobase (kb) fragment was added to the ladder to help identify the bands. Both gels were stained with ethidium bromide and viewed by ultraviolet illumination. FIG. 4A shows a 2% Metaphor agarose gel of the ladder. DNA fragments from 200 bp to 3,000 bp are visible and well resolved. FIG. 4B shows a 1% agarose gel of the 200 bp ladder in the left lane. DNA fragments from 200 bp to 5,000 bp visible are visible and well resolved. The right lane of the ladder shows a 1 kilobase (kb) DNA ladder.

The practice of the invention requires construction of plasmids with restriction sites at specific locations. The placement of restriction sites in a plasmid can be performed in two general manners. In the first method, multiple copies of a DNA segment are cloned into a restriction site of the plasmid vector. The result is a series of restriction sites which are evenly spaced. The preferred approach is to clone the segments so that the segments polymerize in tandem, that is, in a head to tail manner. This is well established in the art by using a nonsymmetrical restriction endonuclease at the ends of the insert segments (Hartley, U.S. Pat. No. 4,403,036). The sticky ends of such segments will only allow polymerization in a head to tail fashion. This first method can also clone a mixture of several differently sized DNA segments. In the second method, restriction sites can be introduced by oligonucleotide site directed mutagenesis using established methods.

It will be appreciated that the length between sites need not be exactly a multiple of the minimum length. Gel electrophoresis cannot resolve fragments which are very close in size. Thus, slight imperfections with the length will not have a noticeable effect on the gel electrophoresis. For example, the 100 bp ladder of FIG. 1 could have a plasmid design with the distance between some sites being 98 bases or 102 bases, instead of 100 bp. The criteria for what constitutes a length which is a considered in this invention as multiple of a minimum length is whether the ladder has acceptably sharp bands for the user. The percent error of length which is acceptable cannot be quantified exactly, since it is a function of the resolving ability of the gel matrix, and the user's subjective criteria for a sharp band. It will also be appreciated that a large length error in one segment may be acceptable if it is the only segment with the error. For example, the 100 bp ladder of FIG. 1 could have a single segment 120 bases long without major band sharpness problems.

It will also be appreciated that the DNA sequence between equally spaced DNA fragments need not be identical. Different sequences are acceptable since agarose gel electrophoresis separates DNA fragments by size, not by sequence. In some cases, improved plasmid stability may result from employing different DNA sequences between the restriction sites.

CONCLUSION

The present invention overcomes the disadvantages of previous methods for making DNA ladders. Previous methods are based on a plasmid design which (i) limits the range of the ladder, and (ii) limits the fraction of the plasmid which generate the ladder. The present invention overcomes these disadvantages with an improved plasmid design. The improved plasmid design (i) allows the ladder fragments to range to the entire plasmid size, and (ii) allows the entire plasmid to generate useful DNA fragments. This invention is classified in a crowded art. There are numerous companies worldwide which manufacture and sell DNA ladders. The present invention represents a significant step forward in the efficient manufacture of DNA ladders.

The method of the invention will now be further described by way of the following, non-limiting examples.

EXAMPLE 1

Plasmid design for 100 base pair ladder

Vector V1 was constructed from plasmid pUC18 by amplifying the origin and ampicillin regions of the plasmid, and deleting the beta-galactosidase region. V1 contains adjacent AvaI and PvuII sites and is exactly 2,000 bp. A DNA fragment was amplified from yeast, cut with AvaI, yielding a 100 bp insert fragment with AvaI sticky ends oriented in the same direction and a single PvuII site adjacent to one AvaI site. Twenty copies of the 100 bp insert were cloned in the AvaI site of V1. The midpoint of the 2 kb vector region of V1 was mutated by PCR mutagenesis to incorporate an additional PvuII site. The resulting plasmid p100 has 21 PvuII sites spaced 100 bp from each other. An additional PvuII site is located exactly 1,000 bp from adjacent PvuII sites. The final design of p100 is illustrated in FIG. 1. The total plasmid size is 4,000 bp. Partial PvuII digestion yields a 100 bp ladder with fragments from 100 bp to 4,000 bp in 100 bp increments. FIG. 2 shows gels separating the DNA fragments of the ladder. A small amount of a 500 bp fragment was added to the ladder to help identify the bands. Both gels were stained with ethidium bromide and viewed by ultraviolet illumination. FIG. 2A shows a 2% Metaphor agarose gel of the ladder. DNA fragments from 100 bp to 2,000 bp are visible and well resolved. FIG. 2B shows a 1% agarose gel of the 100 bp ladder in the left lane. DNA fragments from 400 bp to 4,000 bp visible are visible and well resolved. The right lane of the ladder shows a 1,000 bp ladder.

EXAMPLE 2

Plasmid design for 200 base pair ladder

Plasmid p200 was constructed in a similar manner as plasmid p100, with the following changes: (a) the tandemly repeated DNA insert is 200 bp (instead of 100 bp), and (b) there are 15 tandemly repeated copies of the insert. The total plasmid size is 5,000 bp. The final plasmid design of p200 is illustrated in FIG. 3. Partial PvuII digestion yields a 200 bp ladder with fragments from 200 bp to 5,000 bp in 200 bp increments. FIG. 4 shows electrophoretic gels separating the DNA fragments of the ladder. A small amount of a 1,000 bp fragment was added to the ladder to help identify the bands. Both gels were stained with ethidium bromide and viewed by ultraviolet illumination. FIG. 4A shows a 2% Metaphor agarose gel of the ladder. DNA fragments from 200 bp to 3,000 bp are visible and well resolved. FIG. 4B shows a 1% agarose gel of the 200 bp ladder in the left lane. DNA fragments from 200 bp to 5,000 bp visible are visible and well resolved. The right lane of the ladder shows a 1,000 bp ladder.

I claim:

1. A plasmid for generating DNA ladders, whereby:
   (a) the plasmid contains five or more R sites of a restriction endonuclease R;
   (b) the length between all adjacent R sites is an integer multiple of a minimal length, said minimal length is the length between the closest adjacent R sites;
   (c) partial R restriction endonuclease digestion of the plasmid generates a DNA ladder with at least five differently sized DNA fragments; and
   (d) said DNA ladder has the properties that (i) all DNA fragments of the ladder have lengths which are integer multiples of the minimal length; (ii) the smallest DNA fragment length is the minimal length, (iii) the largest DNA fragment is the length of the entire plasmid; and (iv) the ladder has a DNA fragment at every integer multiple of the minimal length ranging from the minimal length to the plasmid length.

2. A plasmid according to claim 1, wherein the number of R restriction sites is 12 or more, and the number of differently sized DNA fragments is 12 or more.

3. A plasmid according to claim 2, wherein the largest length between adjacent R restriction sites is 25% or less of the total plasmid size.

4. A plasmid according to claim 3, wherein at least 10 of the R restriction sites are equally spaced.

5. A plasmid according to claim 4, wherein the equal spacing length is 100 base pairs.

6. A plasmid according to claim 4, wherein the equal spacing length is 200 base pairs.

7. A plasmid according to claim 4, wherein the equal spacing length is 250 base pairs.

* * * * *